United States Patent [19]

Pink

[11] Patent Number: 4,483,824
[45] Date of Patent: Nov. 20, 1984

[54] METHOD AND APPARATUS FOR LONG-TERM MONITORING OF POLLUTANTS AND MOISTURE IN A FLUID STREAM

[75] Inventor: Hans Pink, Starnberg, Fed. Rep. of Germany

[73] Assignee: Siemens Aktiengesellschaft, Berlin & Munich, Fed. Rep. of Germany

[21] Appl. No.: 434,066

[22] Filed: Oct. 13, 1982

Related U.S. Application Data

[62] Division of Ser. No. 199,946, Oct. 23, 1980, abandoned.

[30] Foreign Application Priority Data

Nov. 16, 1979 [DE] Fed. Rep. of Germany ....... 2946402
Nov. 16, 1979 [DE] Fed. Rep. of Germany ....... 2946424

[51] Int. Cl.$^3$ .............................................. G01N 7/02
[52] U.S. Cl. .......................................... 422/92; 422/83; 422/88; 436/148
[58] Field of Search ................... 310/338; 179/110 A; 73/29, 73, 336.5, 337, 7.4; 422/83, 92, 88; 436/148

[56] References Cited

U.S. PATENT DOCUMENTS

| | | | |
|---|---|---|---|
| 3,029,643 | 4/1962 | Stern | 310/338 |
| 3,479,864 | 11/1969 | Patterson | 73/337 |
| 3,801,838 | 4/1974 | Kistler | 310/338 |
| 4,216,404 | 8/1980 | Kurtz et al. | 310/338 |

*Primary Examiner*—Michael S. Marcus
*Attorney, Agent, or Firm*—Hill, Van Santen, Steadman & Simpson

[57] ABSTRACT

Long-term monitoring of pollutants or moisture in a fluid stream, such as an air stream, is achieved by electrically measuring (and optionally recording) pressure changes caused by a reaction between a pollutant or moisture in the stream and a chemical capable of reacting with such pollutant or moisture. The invention is useful for monitoring apparatus used in environment protection as well as measuring apparatus in determining moisture concentrations in, for example, protective or carrier gas streams utilized in semiconductor technology.

3 Claims, 1 Drawing Figure

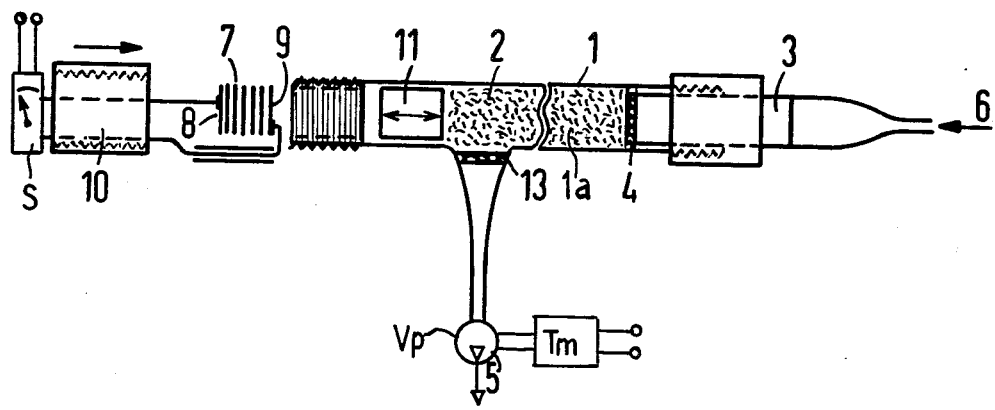

METHOD AND APPARATUS FOR LONG-TERM MONITORING OF POLLUTANTS AND MOISTURE IN A FLUID STREAM

This is a division, of application Ser. No. 199,946, filed Oct. 23, 1980 abandoned.

BACKGROUND OF THE INVENTION

1. Field of the Invention

The invention relates to monitoring selected pollutants or moisture in a fluid stream and somewhat more particularly to a method and apparatus for long-term monitoring of pollutant emissions and pollutant immissions as well as moisture content of various fluid streams, such as an air stream, wherein a chemical reaction or absorption between a pollutant or moisture in the fluid stream with a suitably reactive chemical is utilized as the detection principle and is quantitatively analyzed.

2. Prior Art

A method and apparatus for monitoring gaseous pollutants and/or moisture content of a gas wherein a chemical reaction or absorption between a pollutant or moisture in a gas stream with a solid reaction partner is utilized as a detection principle, is known from the Draeger Test Tube Handbook, 4th Edition, May 1979, Special Publication 2340. The operative principle utilized with the test tubes employed (so-called Draeger tubes), is based on the fact that a chemical compound which is specific for a gas or gaseous component to be detected is emplaced in the tube as a permeable filler material and the tube is then charged with a sucked-in gas stream whereby, corresponding to the concentration of the material being detected and the duration of the sample-taking action (sucked-through air or number of pump strokes, respectively), a discolored zone in the filler column or a lengthened zone of the filler column due to material swelling or expansion, develops. The length of the discolored zone or of the zone which is expanded, respectively, is regarded as the measure of pollutant or moisture concentration respectively. With the foregoing method, gases and vapors, such as hydrogen sulfide, sulfur dioxide, carbon disulfide, carbon monoxide, carbon dioxide, alcohol, benzene, hydrocarbons, nitrous gases and water vapors can be detected and at least partially quantitatively analyzed when one of the foregoing materials or components enters into a specific color reaction with a suitable solid chemical. An example of the foregoing is demonstrated by the reaction:

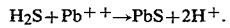

$$H_2S + Pb^{++} \rightarrow PbS + 2H^+.$$

For determination of hydrogen sulfide ($H_2S$), a test tube is filled with a lead-containing preparation as the reagent, which can be applied onto a silic gel carrier and a gas containing $H_2S$ is charged into the tube so as to come into intimate contact with the reagent therein. With the aid of suitably calibrated standards or preparations, the quantity of hydrogen sulfide converted to lead sulfide (with PbS being equalled to the discolored zone) can then be visually determined. For determining water concentration in air, for example, a similar test tube filled with starch or silica gel as the reagent can be utilized.

In addition to the disadvantages of visual determinations, a further disadvantage of the foregoing technique is that remote measurements and time specifications, limitation circuits, etc., coupled therewith are not possible, without a substantial increase in technical outlay.

SUMMARY OF THE INVENTION

The invention provides a method and apparatus for constantly monitoring pollutant and/or moisture concentrations in fluid streams over prolonged periods of time, independent of visual observations.

In accordance with method embodiments of the invention, pollutant emissions, immissions and/or moisture concentrations in a fluid stream are monitored by (a) emplacing a select chemical capable of reacting or absorbing a pollutant or moisture being monitored in a confined space, (b) passing a fluid stream suspected to contain the pollutant or moisture being monitored through such confined chemical whereby when such stream contains the pollutant or moisture, the chemical reacts therewith and undergoes a volume change, (c) converting such volume change into an equivalent pressure change, and (d) electrically measuring (and, optionally, recording) such pressure change.

In certain embodiments of the invention, the above-referenced pressure change is detected by measuring changes in electrical resistance of graphite particles in pressure-transmissive contact with the chemical. Such graphite particles can be in granular form, spherical form or disc form.

In certain other embodiments of the invention, the above-referenced pressure change is determined by a relatively thin diaphragm member composed of a piezo ceramic material operationally connected with the chemical and with an electrical sensor. In yet other embodiments of the invention, the above-referenced pressure change is determined by a semiconductor pressure sensor operationally connected with the chemical and an electrical sensor.

In certain embodiments of the invention, a filter medium capable of absorbing components in a fluid stream disturbing the reaction between the pollutant and/or moisture and the chemical, is positioned in front of the confined spaced containing the chemical and in the passageway directing the fluid stream to such confined space.

Apparatus embodiments of the invention comprise a reactor having a tubular reaction space with a chemical therein capable of reacting with a pollutant or moisture being monitored, a fluid inlet and a fluid outlet in communication with each other via such space, a pressure-sensitive means positioned at an end of the reaction space opposite the fluid inlet and away from the fluid outlet, and an electrical resistance measuring means electrically connected with the pressure-sensitive means and with an indicating means.

In certain embodiments of the invention, the chemical is a solid and in preferred embodiments of the invention, the pollutants are present in a gaseous fluid stream. In certain embodiments of the invention, the above-referenced reaction space is a bent tube. In certain embodiments of the invention, a rigid fluid-permeable wall is provided between the reaction space and the fluid inlet for accommodating a filter medium. In certain embodiments of the invention, the above-referenced reaction space is a flexible, liquid-filled hose or tube and any pressure changes occurring because of a reaction with a pollutant and a suitable chemical, are taken-up by the liquid in the hose and hydraulically transmitted to the measuring means.

In an exemplary apparatus embodiment of the invention, the above-referenced pressure-sensitive means comprises a stack of graphite-disks positioned in pressure-transmissive relation with the chemical in the reaction space, with a first and last disk of such stack being connected to leads for the electrical resistance measuring means.

In certain embodiments of the invention, a vacuum-pump means is operationally connected with the fluid outlet and an elapsed-time meter is coupled with such pump means to measure the total operative time of such pump and thus the total amount of fluid passing through the reaction space. An exemplary form of such elapsed-time meter comprises a capillary tube filled with a copper salt solution and electrically connected to the leads for passing electrical current through the pump means so that during pump operation, an amount of copper is deposited on the interior walls of the tube in accordance with the amount of current passing through the pump and this amount provides a reliable indication of the operating duration of such pump.

BRIEF DESCRIPTION OF DRAWINGS

The FIGURE is an elevated, broken-away, partially exploded, schematic view of an exemplary apparatus useful in the practice of the invention.

DESCRIPTION OF PREFERRED EMBODIMENTS

The invention provides a means of constantly measuring and/or monitoring pollutant or moisture concentrations in a fluid stream, such as an air stream, over prolonged periods of time and independently of visual observations.

In accordance with the principles of the invention, a quantitative analysis of pollutant or moisture concentration in a fluid stream suspected to contain some pollutants or moisture occurs by monitoring volume changes in a chemical which is capable of reacting or absorbing the pollutant or moisture, and which occurs upon contact with such pollutant or moisture, converting such volume change into an equivalent pressure change and electrically sensing (and optionally recording) such pressure change.

In certain preferred embodiments of the invention, the pressure-change brought about by the volume change in a chemical reacting with a pollutant or moisture, is monitored by measuring changes in the electrical resistance of graphite particles positioned in pressure-transmissive contact with such chemical. The graphite particles can be comprised of a relatively small column of graphite granules, a relatively small column of graphite spheres or a relatively small stack of graphite disks.

In certain other embodiments of the invention, the volume change, which occurs because of the reaction between A (pollutant or moisture) with B (a chemical capable of reacting with A) to yield compound AB, is transferred to a relatively thin diaphragm or membrane composed of a suitable piezo-ceramic material, as a consequence of which a defined pressure, varying with progressive reaction or absorption, respectively (i.e., swelling) is exerted on the piezo-ceramic diaphragm, which in turn generates an appropriate signal.

As in other technical applications, such as for example, graphite particles or piezo-ceramic membranes in the speaking piece of a telephone, or stacked graphite disks functioning as current regulators in electrical motors, the electrical resistance change of the graphite particles or the piezo-electric effects of the piezo-ceramic membrane, respectively, are utilized in the practice of the invention for measuring or indicating the varying pressure and hence the progression of the reaction and progress between a pollutant or moisture and a chemical reacting therewith. The selectivity of indication for a substance or pollutant is achieved through the selection of the chemical reaction which takes place in a confined reaction space, i.e., in a form of a tube or the like.

As a further aid to the understanding of the invention, two exemplary reactions between pollutants and suitably reactive chemicals will be explained. These reactions generally comprise (I) the oxidation of iron and (II) the formation of lead sulfide from lead acetate.

Reaction (I) is represented by the equation $$2Fe + 1.5O_2 \rightarrow Fe_2O_3 \qquad (I).$$

When, for example, 112 grams of Fe, which occupies a volume of 14 cm$^3$, reacts with sufficient oxygen, 160 grams of Fe$_2$O$_3$ results, with a volume of 30 cm$^3$ ($\rho_{Fe} = 7.86$, $\rho_{Fe_2O_3} = 5.18$); i.e., in this reaction, a given quantity of the reactable chemical (Fe) about doubles its volume when reacted with a pollutant (O$_2$).

Reaction (II) is represented by the equation:

$$Pb(CH_3COO)_2 + H_2S \rightarrow PbS + 2CH_3COOH \qquad (II).$$

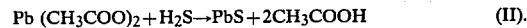

When, for example, 325 grams of lead acetate [Pb(CH$_3$COO)$_2$], which occupies a volume of 100 cm$^3$, is reacted with hydrogen sulfide (H$_2$S), 239.9 grams of lead sulfide (PbS) results, with a volume of only 32 cm$^3$; in the case of this reaction, a reduction of volume to about ⅓ of its initial value occurs in the chemical when reacted with the pollutant.

When one allows a reaction of the foregoing types to run to completion in a tightly enclosed reaction space, i.e., a glass tube having a gas inlet and a gas outlet communicating with the reaction space within the tube, the growing volume produces an increased pressure on the tube walls while a shrinking volume produces a decreased pressure on the tube walls. This change of pressure can be electrically measured and provides a remote means of monitoring the course of the reaction.

In accordance with certain embodiments of the invention, any interfering components or the like in the fluid stream being monitored can absorbed or separated from the fluid stream or a portion thereof being monitored, via a suitable filter.

Further details of the invention will be described in conjunction with the schematically illustrated apparatus, on the basis of two exemplary embodiments, namely the reaction of carbon dioxide with sodium hydroxide asbestos and the absorption or swelling reaction which occurs between water vapor and starch.

A suitable reaction housing 1, which in the embodiment illustrated comprises a straight, relatively thin glass tube, having a reaction space 1a, which is as long as possible in order to extend the pressure build-up zone, which is filled wth a reactive chemical 2, for example, granular sodium hydroxide asbestos particles. Instead of granular sodium hydroxide asbestos, when moisture concentration is being monitored, a suitable water-absorbent, for example, in the form of starch, can be placed in the reaction space 1a.

In instances where the just described reactor form is not possible, for example, because the volume necessary for accommodating the chemical is too small, the pressure change in a large volume can be taken up by a suitable liquid in a flexible hose or the like positioned in the reactor axis and such pressure change can be hydraulically transferred to the measuring system.

The reactor housing is provided wth a fluid inlet 6 and a fluid outlet 5 which communicate with each other via the reaction chamber 1a. A chamber 3 can be provided between the fluid inlet and the fluid outlet and just prior to the reaction space 1a for accommodating a suitable filter material. The chamber 3 must be separated from the reaction space 1a by a rigid, fluid-permeable wall 4 in order that any volume changes, which result also at this location due to interfering materials to be removed from the stream being monitored prior to the reaction between the chemical and the pollutant, cannot falsify the measured pollutant value. The carbon dioxide/air mixture or water/air mixture to be monitored is drawn into the reactor 1 with the aid of a small electrically powered vacuum pump means $V_p$ through the fluid inlet 6 and thus through the chemical positioned within the reaction space 1a.

In certain embodiments, an elapsed-time indicator means $T_m$, is positioned in electrically operating relationship with the pump means $V_p$. In order to prevent the possibility that a too low a value of gas emissions to be monitored may be simulated, due to intermittent operation of the vacuum pump, the operating duration of the pump means is checked by a suitable elapsed-time indicating means. An exemplary form of such an elapsed-time indicator means comprises a capillary tube filled with a copper salt solution and which is electrically connected to the electrical leads providing electricity to the vacuum pump motor so that during operation, a quantity of copper is deposited on the interior walls of the tube, essentially equivalent to the amount of current flowing through the pump motor and thus provides a reliable measure of operating duration.

At an end of the reaction space 1a, sometimes referred to as the pressure build-up zone, a pressure-sensitive means 7 is positioned. In an exemplary embodiment of the invention, such pressure-sensitive means comprises a stack of 25 thin (0.25 mm thick) graphite disks, each having a 9 mm diameter, with the first graphite disk 9 and the last graphite disk 8 being, respectively, connected with platinum wires 8 and 9 which extend out of the tube in an insulated fashion to communicate with a signal indicating means S. The graphite disks are suitably mounted in the end of the reactor housing 1 by means of a threaded cap member 10 and are positioned in pressure-transmissive contact with the reaction space by means of a small freely moveable quartz block 11. Suitably fused fluid-permeable walls 4 and 13 are respectively positioned after the fluid inlet 6 and prior to the fluid outlet so as to limit the reaction space or sample volume in relation to these openings.

After filling the reaction space 1a with a suitable chemical 2, for example, granular sodium hydroxide asbestos particles or starch, through adjustment of the threaded cap member 10, the pressure on the pressure-sensitive means 7, for example, the graphite disks, is arbitrarily adjusted to a fixed value. The electrical resistance measured in this state between the platinum wires 8 and 9 is regarded as the initial output resistance, $R_O$. Then a dry $CO_2$/air mixture or a water-vapor/air mixture to be monitored, is fed through the reactor housing 1 and the resistance changes thus occurring is measured.

Sodium hydroxide asbestos is composed of asbestos fibers having embedded therein sodium hydroxide. This material reacts with carbon dioxide in accordance with the equation:

$$2\ NaOH + CO_2 \rightarrow Na_2CO_3 + H_2O \qquad (III).$$

From 2 moles of NaOH (which is equal to 80 grams) reacting with one mole of $CO_2$ (which is equal to 44 grams) there results one mole of $Na_2CO_3$ (which is equal to 106 grams) and 1 mole of $H_2O$ (which is equal to 18 grams). Taking into account the density difference between NaOH ($\rho_{NaOH}=2.130$ g/cm$^3$) and $Na_2CO_3$ ($\rho_{Na_2CO_3}=2.532$ g/cm$^3$), in a case of a molar conversion of 170.4 cm$^3$ to 268.4 cm$^3$ (+18 cm$^3$H$_2$O), the volume change which occurs corresponds to about a 68% increase in volume. This value is calculated for pure sodium hydroxide for sodium hydroxide asbestos, it is somewhat lower on account of the "dilution" due to the asbestos fibers.

In the above-described arrangement, a decrease in the initial output resistance $R_0$, adjusted prior to the reaction, was measured after reaction with carbon dioxide. The amount of the decrease in $R_0$ was found in parallel experiments, with a two-hour reaction time each to be 2 $\Omega$. This minor effect can be attributed to the fact that the relatively elastic asbestos fibers act as a buffer in that they absorb the pressure build-up during the volume enlargement so that the volume enlargement is only partially employed in compressing the graphite disk stack.

Instead of a stack of graphite disks, a piezo-ceramic member or a semi-conductor member can be utilized as the pressure-sensing means.

Since the reaction within a reactor is, in each instance, specific for one pollutant (for example, selected from the group consisting of hydrogen sulfide, carbon dioxide, carbon monoxide, hydrocarbons, sulfur dioxide, nitrous gases, $NO_x$, arsenic hydride, water vapor etc.,) the reaction space within such reactor is filled with a suitable chemical or reagent (for example, selected from the group consisting of lead compounds, barrium hydroxide, iodine pentoxide, selenium dioxide with thiosulphuric acid, disodium tetrachloromercurate, chromium (VI)-compounds, gold compounds, etc.,) and each reactor is randomly exchangeable with other like apparatus constructed and operable in accordance with the principles of the invention so that a plurality of fluids, gases or vapors can be remotely monitored via appropriate electrical signals. The principles of the invention, as compared with the earlier-referenced Draeger tubes which have a complicated structure and are based on the effects of chromatography, allow one to take remote measurements, provide time specification, limitation circuits, etc.

Further, in accordance with the principles of the invention, a plurality of moisture-containing substances, for example, protective or carrier gases used in semiconductor technology, can be monitored for their respective moisture concentration and this value can be converted into electrical signals, which can be recorded, if desired, or be utilized or control other process parameters.

As is apparent from the foregoing specification, the present invention is susceptible of being embodied with various alternations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

I claim as my invention:

1. An apparatus for long-term monitoring of select pollutants and/or moisture in a fluid stream comprising:
   a reaction housing having an internal tubular confinable reaction space filled with a chemical capable of reacting with a select pollutant and/or moisture;
   a fluid inlet and a fluid outlet defined in said housing and positioned in spaced relationship to one another, said inlet and outlet being in communication with each other via said reaction space;
   a pressure-sensitive sensing means positioned in one end region of said reaction space in a generally opposed relationship to said fluid inlet and in spaced relationship to said fluid outlet and in a pressure sensing relationship to said chemical in said space;
   an electrical resistance measuring means operationally associated with said pressure-sensitive sensing means;
   an electrically powered vacuum pump means operationally associated with said fluid outlet; and
   an elapsed-time indicator means functionally associated with said pump means for measuring the total operative time of said pump means;
   said elapsed-time indicator or means comprising a capillary tube containing a copper salt solution therein, said capillary tube being electrically connected to leads passing electrical current to said pump means whereby, during operation of said pump means, an amount of copper is deposited on interior walls of said capillary tube in accordance with the amount of current passing through said pump means.

2. An apparatus as defined in claim 1 wherein a fluid-permeable rigid wall is positioned within said reaction housing between said reaction space and said fluid inlet and located so as to define a chamber for a filter layer.

3. An apparatus as defined in claim 1 wherein said pressure-sensitive sensing means comprises a stack of graphite disks positioned in pressure-transmissive relation with said chemical in said space with a first and last disk of said stack being connected to electrically conductive leads communicating with said measuring means.

* * * * *